United States Patent [19]

Nakagawa

[11] Patent Number: 5,314,823
[45] Date of Patent: May 24, 1994

[54] METHOD FOR CLEANING A CONTACT LENS

[75] Inventor: Akira Nakagawa, Nagoya, Japan

[73] Assignee: Tomei Sangyo Kabushiki Kaisha, Nagoya, Japan

[21] Appl. No.: 963,671

[22] Filed: Oct. 20, 1992

[30] Foreign Application Priority Data

Sep. 10, 1992 [JP] Japan .................. 4-268156

[51] Int. Cl.$^5$ .............. D06M 16/00; C02F 5/00; C11D 3/00
[52] U.S. Cl. ............... 435/264; 252/174.12; 252/80; 252/82
[58] Field of Search .......... 435/264; 252/174.12, 252/80, 82; 514/839, 840

[56] References Cited

U.S. PATENT DOCUMENTS

| | | | |
|---|---|---|---|
| 3,910,296 | 10/1975 | Karageozian et al. | 134/2 |
| 4,096,870 | 6/1978 | Manfuso | 134/28 |
| 4,865,983 | 12/1989 | Durham | 435/264 |

FOREIGN PATENT DOCUMENTS

| | | |
|---|---|---|
| 0384666 | 8/1990 | European Pat. Off. |
| 0462460 | 12/1991 | European Pat. Off. |
| 508381 | 10/1992 | European Pat. Off. |
| 2854278 | 7/1980 | Fed. Rep. of Germany |
| 5031834 | 12/1978 | Japan |
| 54-140553 | 10/1979 | Japan |
| 62-250413 | 10/1987 | Japan |
| 1180515 | 7/1989 | Japan |
| 2168224 | 6/1990 | Japan |
| 4-51015 | 2/1992 | Japan |
| 493919 | 3/1992 | Japan |
| 4143718 | 5/1992 | Japan |
| 4161921 | 6/1992 | Japan |

OTHER PUBLICATIONS

Hioki, S. Abstract of Japanese Unexamined Patent Application 62-70812, published Mar. 1, 1987.
Nakagawa, A. et al. Abstract of Japanese Unexamined Patent Application 04-51015, published Feb. 19, 1992.
Nakagawa, et al. Chemical Abstract CA118(14):127013s of EP 508381A2, published Oct. 14, 1992.
ICLC, vol. 15, pp. 256-259, 1988, D. Dea, et al., "The Effect of Reducing Agents On Enzymatic Cleaning Efficacy".

*Primary Examiner*—Michael G. Wityshyn
*Assistant Examiner*—Timothy J. Reardon
*Attorney, Agent, or Firm*—Oblon, Spivak, McClelland, Maier & Neustadt

[57] ABSTRACT

A method for cleaning a contact lens, which comprises diluting an enzyme-containing aqueous solution containing an effective amount of serine protease and from 30 to 95% by weight of glycerol with a diluting solution containing from 0.05 to 5% by weight of an anionic surfactant having no polyoxyethylene glycol unit and from 0.005 to 0.1% by weight of ethylenediamine tetraacetate to a glycerol concentration of not higher than 5% by weight, to obtain a treating solution, and immersing a contact lens in the treating solution.

9 Claims, No Drawings

METHOD FOR CLEANING A CONTACT LENS

The present invention relates to a method for cleaning a contact lens by means of a liquid cleaning agent. Particularly, it relates to a method for cleaning a water non-containing contact lens simply and very efficiently.

Contact lenses are generally classified into those made of water containing material and those made of water non-containing material. As water non-containing contact lenses, those made essentially of polymethyl methacrylate or silicone rubber, and those made of an oxygen-permeable copolymer of polysiloxanyl methacrylate with methyl methacrylate, are known. When such contact lenses are put on the eyes, lipids derived from e.g. sebum as well as proteins and inorganic substances such as calcium in lacrimae tend to deposit thereon. Therefore, it has been common to clean contact lenses with a cleaning agent containing a protease.

Such a protease to be used for cleaning contact lenses is very unstable in a solution. Therefore, it has been common to supply it in the form of a solid formulation such as tablets or granules, so that the user may use it by dissolving the solid formulation in e.g. purified water, as the case requires, about once in a week. However, in recent years, it has been proposed to use a liquid cleaning agent having an enzyme such as protease stabilized in a liquid, in order to eliminate cumbersomeness to dissolve a solid enzyme.

For example, Japanese Unexamined Patent Publications No. 180515/1989, No. 168224/1990, No. 93919/1992, No. 3718/1992 and No. 161921/1992 propose cleaning agents and cleaning methods wherein a liquid agent having a protease incorporated in an organic liquid miscible with water, such as a polyhydric alcohol, is applied to a contact lens to clean it by rubbing, or a contact lens is immersed in a solution obtained by diluting the liquid agent with an aqueous medium. As the aqueous medium, purified water, a physiological sodium chloride aqueous solution or a contact lens cleaning solution containing a surfactant is thereby used. Further, Japanese Unexamined Patent Publication No. 51015/1992 proposes a cleaning and preserving solution for contact lenses, wherein a protease is stabilized by a combination of a polyhydric alcohol, an alkali metal salt and a surfactant.

However, it has been found that in any one of these liquid agents, the polyhydric alcohol used as a stabilizer for the enzyme prevents the protein-removing activity of the enzyme, and no adequate cleaning effects can be obtained. Even when such liquid agents are diluted with an aqueous medium, the action by the protease is inadequate to remove the soil fixed to the contact lens, and it has been difficult to sufficiently remove such fixed soil. Therefore, when these liquid enzyme cleaning agents are employed, it has been necessary to clean lenses every day. An oxygen-permeable contact lens may be continuously worn for one week. Nevertheless, it has been obliged to clean the contact lens every day to remove such fixed soil.

On the other hand, some technical studies have been made to improve the cleaning effects by improving the protein removing activity of an enzyme. For example, Japanese Unexamined Patent Publication No. 31834/1975 proposes a cleaning method which comprises contacting a contact lens to a solution containing a protease such as papain and a sulfurhydryl group-containing compound. This sulfurhydryl group-containing compound serves as a stabilizer for a thiol protease such as papain, and it is known to increase the activity of an enzyme by reducing the soil component, as reported in "ICLC, Vol. 15, p.256-259, 1988". However, this sulfurhydryl group-containing compound is unstable in an aqueous solution, and it has a problem that it is difficult to supply it in the form of solution.

Further, Japanese Unexamined Patent Publication No. 140553/1979 discloses a cleaning agent having urea and a guanidine salt added to the above-mentioned protease and the sulfurhydryl group-containing compound. However, also in this method, it has been difficult to supply the cleaning agent in the form of a solution, and the urea or the guanidine salt does not provide adequate effects unless it is at a sufficiently high concentration. Therefore, this method is not advantageous from the economical viewpoint. Further, this method does not provide adequate cleaning effects against a lipid soil.

Japanese Unexamined Patent Publication No. 250413/1987 proposes a method for improving the cleaning effects by mixing papain with a linear anionic surfactant. However, the activity of such an anionic surfactant is specific to papain, and such papain can hardly be supplied in a liquid state because of the problem of a stabilizer as mentioned above.

The present invention has been made under these circumstances, and it is an object of the present invention to obtain a high protein-removing effect by means of a liquid enzyme cleaning agent and thus to make it possible to clean contact lenses simply and efficiently and to obtain an excellent cleaning effect also against a firmly fixed soil.

To solve the above problems, the present inventors have conducted an extensive research for a method for effectively conducting cleaning of contact lenses by a liquid cleaning agent containing a protease and have studied the most effective method in a process which comprises diluting with a diluting solution, an enzyme-containing aqueous solution having an enzyme stabilized in a solution to obtain a treating solution and immersing a contact lens in the treating solution. As a result, it has been found that in order to obtain a high cleaning effect, the components of the enzyme-containing aqueous solution and the diluting solution and the concentration of the components when they are mixed, are important. And, it has been found that it is important to use glycerol as a stabilizer for an enzyme in an enzyme-containing aqueous solution and to incorporate an anionic surfactant having no polyethylene glycol unit and ethylenediamine tetraacetate to the diluting solution, and further it is important to bring the glycerol concentration to a level of not higher than 5% by weight when a treating solution is prepared by diluting the enzyme-containing aqueous solution with the diluting solution.

Thus, the present invention has been accomplished on the basis of the above discoveries, and it provides a method for cleaning a contact lens, which comprises diluting an enzyme-containing aqueous solution containing an effective amount of serine protease and from 30 to 95% by weight of glycerol with a diluting solution containing from 0.05 to 5% by weight of an anionic surfactant having no polyoxyethylene glycol unit and from 0.005 to 0.1% by weight of ethylenediamine tetraacetate to a glycerol concentration of not higher than 5% by weight, to obtain a treating solution, and immersing a contact lens in the treating solution.

In the present invention, the treating solution for a contact lens is preferably prepared by diluting the above-mentioned enzyme-containing aqueous solution with a diluting solution containing from 0.05 to 5% by weight of an anionic surfactant having no polyoxyethylene unit, from 0.005 to 0.1% by weight of ethylenediamine tetraacetate and from 0.2 to 5% by weight of a copolymer of isobutylene with maleic anhydride or a copolymer of methyl vinyl ether with maleic anhydride.

In the present invention, glycerol used as a stabilizer for the enzyme in the enzyme-containing aqueous solution has a characteristic such that it not only stabilize the enzyme but also does not adversely affect the protein removing activity by the enzyme. Further, the anionic surfactant having no polyoxyethylene glycol unit and the ethylenediamine tetraacetate incorporated to the diluting solution, have synergistic effects to improve the protein removing activity by the enzyme. Namely, in the present invention, a component which impairs the protein removing activity by the enzyme, is eliminated and at the same time, a component which improves the protein removing activity by the enzyme is incorporated. Further, in the present invention, when the treating solution is prepared by diluting the enzyme-containing aqueous solution with the diluting solution, the glycerol concentration in the treating solution is adjusted to a concentration not to impair the protein removing activity by the enzyme i.e. to a level of not higher than 5% by weight. By the combination of these features, the protein removing activity by the enzyme is improved extremely effectively, whereby cleaning of a contact lens with the liquid agent can be conducted simply and efficiently, and even a firmly fixed soil can advantageously be removed.

In the present invention, cleaning is usually conducted by immersing the contact lens in the treating solution. In a case where a lipid soil or the like is cleaned by rubbing, it is advisable to preliminarily add a viscosity-increasing agent to the diluting solution in order to improve the handling efficiency of the treating solution. In such a case, as a thickener which provides an excellent lubricating property without impairing the protein removing activity by the enzyme, a copolymer of isobutylene with maleic anhydride or a copolymer of methyl vinyl ether with maleic anhydride is particularly advantageously selected.

Now, the present invention will be described in detail with reference to the preferred embodiments.

To the enzyme-containing aqueous solution to be used in the present invention, a protease and a stabilizer for the enzyme are incorporated. Proteases are generally classified into four types of serine protease, thiol protease, metal protease and carboxy protease depending upon their active sites. In the present invention, serine protease is used among them. It is particularly preferred to employ serine protease derived from bacteria belonging to Bacillus among those derived from microorganisms, since it has a relatively better stability in the solution.

Further, recently, serine proteases having the stability further improved by genetic engineering have been commercially available, and such proteases may also be suitably used in the present invention. Specifically, Bioprase (manufactured by Nagase Seikagaku Kogyo K.K.), Alkalase, Esperase, Savinase, Durazyme, Subtilisin A (manufactured by Novo Nordisk Bioindustry Japan K.K.), Protease N "Amano" and Protease S "Amano" (manufactured by Amano Pharmaceutical K.K.) may be mentioned.

Such a protease is incorporated in an effective amount, which is usually from 0.001 to 10% by weight. If the concentration is lower than this range, it tends to be difficult to obtain adequate protein-removing effects. On the other hand, if it exceeds this range, no further improvement in the protein removing effects can be expected, and not only that, a possible danger to the eye increases. Such an enzyme is incorporated preferably in an amount of from 0.01 to 5% by weight.

To stabilize such a protease in the enzyme-containing aqueous solution, a stabilizer for the enzyme is incorporated. As such a stabilizer, a compound containing many oxygen atoms or hydroxyl groups in its molecule has been employed. The oxygen atoms or hydroxyl groups of such a compound are believed to form hydrogen bonds with polar groups on the surface of the enzyme protein molecule to stabilize the three dimensional structure of the enzyme molecule. However, such a stabilizer interacts with the enzyme, and thereby impairs the protein removing activity of the enzyme when the enzyme is applied to remove the soil on the lens. Thus, there has been a problem that no adequate protein removing effects can be obtained.

From the actual study of the relation between the enzyme-stabilizing effects and the adverse effects against the protein removing activity with respect to various enzyme stabilizers, it has been found that bivalent alcohols such as ethylene glycol, diethylene glycol, polyethylene glycol and propylene glycol, sugar alcohols such as sorbitol, mannitol and erythritol and saccharides such as fructose, glucose and maltose all strongly inhibit the protein removing activity by an enzyme not only at a high concentration where they exhibit enzyme-stabilizing effects but also when they are diluted to a concentration suitable for cleaning operation.

Whereas, it has been unexpectedly found that glycerol exhibits a high level of enzyme-stabilizing effects and does not inhibit the protein removing activity by an enzyme when diluted to a concentration suitable for cleaning operation. On the basis of this discovery, in the present invention, glycerol is used as an enzyme-stabilizing agent. The enzyme stability is not good if the glycerol concentration is too high or too low. Therefore, in the present invention, glycerol is used in an amount of from 30 to 95% by weight, preferably from 50 to 80% by weight. To such an enzyme-containing aqueous solution, a water-soluble calcium salt may be added in an amount not higher than 0.05% by weight, preferably not higher than about 0.01% by weight, in order to further improve the stability of the enzyme, as the case requires. As such a water-soluble calcium salt, calcium chloride, calcium nitrate or calcium acetate may suitably be employed.

The enzyme has a specific pH range in which it is stable. In the present invention, the pH of the enzyme-containing aqueous solution is preferably maintained within a range of from 6 to 9. For this purpose, from 0.1 to 10% by weight of a buffer solution is usually employed. Specifically, triethanol amine-hydrochloric acid or acetic acid, or tris(hydroxymethyl)aminomethanehydrochloric acid may suitably be employed.

Such an enzyme-containing aqueous solution has a high osmotic pressure by the incorporation of glycerol and thus has a preservative effect to some extent. However, when a higher preservative effect is required, a preservative may be added. Such a preservative is selected from those which are highly safe and which do not adversely affect the contact lens material. For example, potassium sorbate, sodium benzoate, a methyl ester, ethyl ester or propyl ester of benzoic acid, a 5,5-dimethylhydantoin-formaldehyde condensation product, benzyl alcohol, an alkyldiaminoethylglycin hydrochloride, di(aminopropyl)laurylamine, laurylaminopropionic acid and lauryldimethylamino acetic acid betaine may be mentioned. The amount of such preservative varies depending upon the required antiseptic effects, but is usually within a range of from 0.0001 to 5% by weight.

Such an enzyme-contaning aqueous solution is diluted in such a manner that from one to a few drops thereof are dropped to a diluting solution which will be described hereinafter. However, splitting of the liquid drop tends to be poor sometimes due to an increase of the viscosity by glycerol added as the stabilizer for the enzyme. To prevent such a tendency, a small amount of a surfactant may be added to the enzyme-containing aqueous solution. Specifically, an anionic surfactant having no polyoxyethylene glycol unit may be added in an amount of not more than 2% by weight, and a nonionic surfactant may also be added in an amount not exceeding such an anionic surfactant. If an anionic surfactant having polyoxyethylene glycol units is used, or if a nonionic surfactant is present in an amount exceeding the anionic surfactant, cleaning effects of the treating solution prepared by diluting such a solution with a diluting solution which will be described hereinafter, tend to deteriorate.

On the other hand, the diluting solution to be used in the present invention contains an anionic surfactant having no polyoxyethylene glycol unit and ethylenediamine tetraacetate. By the action of these components, the protein removing activity by the enzyme will be synergistically increased.

Specific examples of the anionic surfactant having no polyoxyethylene glycol unit include an $\alpha$-olefin sulfonate, an alkyl sulfonate, an alkylbenzene sulfonate, an N-acylamino acid salt and an alkyl sulfocarboxylate. More specifically, sodium tetradecene sulfonate, sodium dodecyl sulfonate, triethanol amine dodecyl sulfonate, sodium dodecylbenzene sulfonate, sodium dioctylsulfosuccinate, sodium cocoilsarcosine, and sodium lauroylsarcosine, may be mentioned. Such an anionic surfactant is used usually in an amount of from 0.05 to 5% by weight. If the amount is less than this range, the synergistic effect for improving the protein removing activity by an enzyme tends to be low. On the other hand, if the amount exceeds this range, no further improvement in the effect will be obtained. Preferably, such an anionic surfactant is used within a range of from 0.1 to 2% by weight. The reason why such an anion surfactant having no polyoxyethylene glycol unit specifically improve the protein removing activity of the enzyme among various surfactants, is not clearly understood. However, the following mechanism can be assumed. Firstly, when the protease acts on a protein soil deposited on the lens surface, there will be steric hindrance. Here, by the addition of an anionic surfactant which is generally excellent in the permeability and modifying action to a protein, the protein soil is believed to be modified, and penetration of the enzyme is believed to be facilitated. However, polyoxyethylene glycol units are believed to interact with the enzyme or the protein soil due to oxygen atoms or hydroxyl groups in its molecule and thus impair the activity of the enzyme. Thus, an anionic surfactant having no polyoxyethylene glycol unit is believed to specifically improve the activity of the enzyme to remove the protein from the lens. Therefore, in the present invention, the one having polyoxyethylene glycol units can not be used even if it is an anionic surfactant.

The ethylenediamine tetraacetate to be incorporated in the diluting solution is a component having a chelating activity to inorganic substances and serves to synergistically improve the protein removing activity by the enzyme together with the anionic surfactant, by removing an inorganic soil such as calcium complexed with the protein soil. Specifically, it may, for example, be disodium ethylenediamine tetraacetate dihydrate or tetrasodium ethylenediamine tetraacetate tetrahydrate. It is used usually in an amount of from 0.001 to 0.1% by weight. If the amount is less than this range, the effect for synergistically improve the protein removing activity by the enzyme tends to be low. On the other hand, if it exceeds this range, no further improvement in the effect will be obtained. Such a synergistic protein removing effect by such a metal chelating agent is specific to the ethylenediamine tetraacetate, and the effect is rather low with other metal chelating agent such as a nitrilotriacetate, a gluconate or a succinate, and no effect is observed with a salt of phosphoric acid such as pyrophosphoric acid, tripolyphosphoric acid or tetrapolyphosphoric acid.

The desired diluting solution can be obtained by mixing the above described components. However, the soil deposited on a contact lens includes lipids in addition to proteins. In order to improve the cleaning effect against such lipids, a nonionic surfactant may also be incorporated. However, if a nonionic surfactant is added in an amount larger than the above-mentioned anionic surfactant, it tends to impair the synergistic effect of the anionic surfactant to improve the cleaning effects of the enzyme, although the cleaning effects against lipids may be improved. Therefore, the nonionic surfactant may not be added in an amount exceeding the above anionic surfactant. Specific examples of such a nonionic surfactant include a polyoxyethylenealkylphenyl ether, a polyoxyethylene-polyoxypropylene-block polymer, a polyoxyethylenealkyl ether, an alkanol amide, and a polyoxyethylene sorbitane fatty acid ester, although the nonionic surfactant is not limited to such specific examples.

Further, a thickener may be added to such a diluting solution taking into consideration a possibility of removing a lipid soil by rubbing. Such a viscosity-increasing agent is preferably the one which provides an excellent lubricating property without impairing the protein removing activity by the enzyme. For this purpose, a copolymer of isobutylene with maleic anhydride or a copolymer of methyl vinyl ether with maleic anhydride is used particularly preferably in the present invention. The amount is preferably within a range of from 0.2 to 5% by weight. If the amount is less than 0.2% by weight, the lubricating property will not be improved. On the other hand, if the amount exceeds 5% by weight, the viscosity tends to be too high and cleaning tends to be difficult.

Further, a preservative may be used, as the case requires, for the purpose of preventing proliferation of bacteria in the diluting solution. Specifically, it may be the same component as used for the enzyme-containing aqueous solution. Further, such a diluting solution is preferably adjusted to a pH range which is mild to the eyes and which is suitable for the action of the enzyme. For this purpose, a suitable buffer solution may be used. Specifically, the pH is adjusted to a level within a range of from 7 to 9.5. To prepare a treating solution by diluting the above described enzyme-containing aqueous solution with the diluting solution thus obtained, the glycerol concentration in the treating solution is adjusted to a level of not higher than 5% by weight. If the glycerol concentration is high, there will be an adverse effect of glycerol to the protein removing activity. Preferably, the enzyme-containing aqueous solution is diluted to a glycerol concentration of not higher than 3% by weight. If the diluting rate is too high, the enzyme concentration in the treating solution tends to be too low, and the protein removing activity tends to be inadequate. Therefore, the diluting rate for diluting the enzyme-containing aqueous solution with the diluting solution is set at a level of from about 6 to 400 times, preferably from about 10 to 200 times.

For the preparation of the treating solution, a storage case for a contact lens which is commonly used, may be employed. Namely, the diluting solution is filled in the storage case, and from one to three drops of the enzyme-containing aqueous solution may simply be dropwise added thereto. Then, a contact lens is held by a holder and immersed in the storage case for a predetermined period of time, whereby cleaning can be done. The time for immersion varies depending upon the degree of the soil on the contact lens. Specifically, the contact lens is immersed from one minutes to 24 hours, preferably from 10 minutes to 2 hours, within a temperature range of from 5° to 40° C. The cleaning effects tend to be high as the temperature increases. However, in the present invention, cleaning can effectively be conducted even at a low temperature at a level of 5° C. At a temperature of lower than 5° C., no adequate cleaning effect can be obtained. On the other hand, if the temperature is higher than 40° C., an adverse effect to the contact lens tends to result. After completion of such cleaning, the contact lens is taken out, rinsed with tap water, purified water or a physiological sodium chloride aqueous solution and then used as it is.

By such a cleaning method, the protein removing activity by the enzyme is improved extremely effectively. Therefore, very high cleaning effects can be obtained in spite of the fact that a liquid enzyme cleaning agent is used, and cleaning of a contact lens can be conducted simply and efficiently. Further, according to the present invention, even a contact lens continuously worn for one week can effectively be cleaned.

Now, the present invention will be described in further detail with reference to typical Examples. However, it should be understood that the present invention is by no means restricted by such specific Examples. Further, it should be understood that in addition to the above-described specific embodiments and the following Examples, various changes, modifications or improvements may be made to the present invention without departing from the spirit of the present invention on the basis of the common knowledge of those skilled in the art.

Preparation of the enzyme-containing aqueous solutions

The respective components were weighed in the proportions as identified in the following Table 1, and various enzyme-containing aqueous solutions (hereinafter referred to enzyme solutions) A to C were prepared. Each enzyme solution was stored at a temperature of 40° C. for 6 months, whereupon the ratio of the remaining activity to the protease activity at the time of the preparation was obtained. The results are shown also in Table 1.

The protease activity was measured as follows.

Firstly, 1 ml of a treating solution prepared by diluting each enzyme solution with purified water, was added to 5 ml of a 0.6% casein solution (pH 7, a 0.05M sodium monohydrogen phosphate aqueous solution) maintained to 37° C., and the mixture was incubated at 37° C. for 10 minutes. Then, 5 ml of a precipitating reagent solution (a mixed solution comprising 0.11M trichloroacetic acid, 0.22M sodium acetate and 0.33M acetic acid) was added thereto to precipitate non-decomposed proteins, followed by filtration. With respect to the filtrate thereby obtained, absorption A at 275 nm was obtained. Separately, 5 ml of the above precipitating reagent solution was added to 1 ml of the above treating solution prepared by diluting each enzyme solution with purified water. Then, the above casein solution was added thereto, and the formed precipitate was filtered off. With respect to the filtrate, absorption $A_0$ at 275 nm was obtained. By the following formula, the protease activity was obtained, and the remaining activity (%) was further obtained. An enzymatic activity capable of forming a non-protein substance showing an absorption at 275 nm in an amount corresponding to $1 \times 10^{-6}$ g of tyrosine per minute, was evaluated to be 1 u.

Protease activity
$(u/ml) = [(A - A_0)/A_s] \times 50 \times (11/10) \times$ diluting times of the enzyme solution at the time of analysis where $A_s = 0.391$ (absorption by 50.0 µg/ml of tyrosine at 275 nm)

Remaining activity (%) = [(protease activity after storage at 40° C. for 6 months/protease activity at the time of preparation)] × 100

TABLE 1

|  |  | Enzyme solution | | |
|---|---|---|---|---|
|  |  | A | B | C |
| Components (g) | Glycerol | 50 | 78 | 75 |
|  | Purified water | 42.4 | 15.3 | 17.3 |
|  | CaCl$_2$.2H$_2$O | 0.05 | 0.01 | — |
|  | Triethanolamine | 5 | 5 | 5 |
|  | Hydrochloric acid | — | 0.7 | 0.7 |
|  | Acetic acid | 1.4 | — | — |
|  | Esperase*[1] | 1.0 | 1.0 | — |
|  | Subtilisin A*[2] | — | — | 2.0 |
|  | Sodium benzoate | 0.2 | — | — |
| Remaining activity after storage at 40° C. for 6 months | | 94% | 100% | 95% |

Note: *[1], *[2]: Proteases derived from Bacillus, manufactured by Novo Nordisk Bioindustry Ltd.

Preparation of the diluting solutions

The respective components were weighed in accordance with the following Table 2 and dissolved in purified water so that the total amount would be 100 g. Then, the pH was adjusted by sodium hydroxide or hydrochloric acid to the respective levels as shown in Table 2, to obtain diluting solutions a to g.

TABLE 2

| | | Diluting solution | | | | | | |
|---|---|---|---|---|---|---|---|---|
| | | a | b | c | d | e | f | g |
| Surfactant (g) Anionic | Neopelex F25[*1] | 0.5 | — | — | — | — | — | 1.50 |
| | Rapizol C-70[*2] | — | 1.0 | — | — | — | — | — |
| | TEALS[*3] | — | — | 2.5 | — | — | — | — |
| | Sulcosinate LN30[*4] | — | — | — | 5.0 | — | — | — |
| | OS-14[*5] | — | — | — | — | 0.75 | 0.75 | — |
| Nonionic | Nonion HS-220[*6] | — | — | — | — | — | 0.50 | — |
| | Pronone 204[*7] | — | — | — | — | — | — | 1.0 |
| Viscosity-increasing agent (g) | Isoban 110[*8] | 0.5 | 0.2 | — | 2.5 | — | 0.5 | — |
| | GANTREZ AN[*9] | — | — | 2.0 | — | — | — | 0.5 |
| Chelating agent (g) | Crewat N[*10] | 0.01 | 0.02 | 0.05 | 0.1 | 0.05 | 0.03 | 0.05 |
| Preservative (g) | Glydant[*11] | — | 0.02 | — | 0.02 | — | 0.02 | — |
| pH | | 6.5 | 7.0 | 7.5 | 8.0 | 8.5 | 9.0 | 9.5 |

[*1]: Sodium dodecylbenzenesulfonate, manufactured by Kao Corporation
[*2]: Sodium dioctylsulfosuccinate, manufactured by Nippon Oil & Fats Co., Ltd.
[*3]: Triethanolamine laurylsulfate, manufactured by Nikko Chemicals Co., Ltd.
[*4]: Sodium lauroylsulcosine, manufactured by Nikko Chemicals Co., Ltd.
[*5]: Sodium α-olefin sulfonate, manufactured by Nikko Chemicals Co., Ltd.
[*6]: Polyoxyethylene(20)octylphenyl ether, manufactured by Nippon Oil & Fats Co., Ltd.
[*7]: Polyoxyethylene-polyoxypropylene blockpolymer, manufactured by Nippon Oil & Fats Co., Ltd.
[*8]: Copolymer of isobutylene with maleic anhydride, manufactured by Kuraray Co., Ltd.
[*9]: Copolymer of methyl vinyl ether with maleic anhydride, manufactured by Gokyo Sangyo K.K.
[*10]: Disodium ethylenediamine tetraacetate dihydrate, manufactured by Teikoku Kagaku Sangyo K.K.
[*11]: 1,3-dimethylol-5,5-dimethylhydantoin, manufactured by Ronza

Test for protein removing effects

Firstly, an aqueous solution containing 0.2% by weight of lysozyme and 0.01% by weight of calcium chloride (dihydrate) was adjusted to pH11 by sodium hydroxide, and an oxygen permeable hard contact lens (Menicon EX, manufactured by Menicon Co., Ltd.) was soaked at 37° C. for three days. Then, this lens was rubbed with fingers for cleaning and rinsed with tap water, and then it was observed by a dark-field microscope under 10 magnifications, whereby deposition of a protein soil was observed over the entire lens. Using such a soiled lens, the following test for protein removing effects was conducted.

Namely, firstly, the above-mentioned enzyme solutions A to C were respectively diluted with the above-diluting solutions a to g as shown in the following Table 3 to obtain various treating solutions No. 1 to No. 9. Then, each treating solution was put into a storage case for a contact lens. On the other hand, the above soiled lens was held by a lens holder and set in this storage case. In such a storage case, the soiled lens was soaked in each treating solution at 20° C. for 30 minutes. Then, the lens was taken out and observed by a dark-field microscope and evaluated in accordance with the following standards. As a result, in a case where any one of the treating solutions No. 1 to 9 was used, a soil deposited on the lens was completely removed, with Evaluation 6.

| | |
|---|---|
| The entire lens is awfully turbid | Evaluation 1 |
| The entire lens is turbid | Evaluation 2 |
| Turbidity of the lens remains at least 50% | Evaluation 3 |
| Turbidity of the lens remains at least 10% | Evaluation 4 |
| Lens is slightly turbid | Evaluation 5 |
| No turbidity of the lens was observed | Evaluation 6 |

TABLE 3

| | | Treating solution No. | | | | | | | | |
|---|---|---|---|---|---|---|---|---|---|---|
| | | 1 | 2 | 3 | 4 | 5 | 6 | 7 | 8 | 9 |
| Enzyme solution (g) | A | 0.1 | — | — | — | — | — | 0.025 | — | — |
| | B | — | 0.1 | — | 0.05 | 0.05 | 0.05 | — | 0.025 | — |
| | C | — | — | 0.1 | — | — | — | — | — | 0.025 |
| Diluting solution (g) | a | 2.5 | — | — | — | — | — | — | — | — |
| | b | — | 2.5 | — | — | — | — | — | — | — |
| | c | — | — | 2.5 | — | — | — | — | — | — |
| | d | — | — | — | 2.5 | — | — | — | — | — |
| | e | — | — | — | — | 2.5 | — | — | — | 2.5 |
| | f | — | — | — | — | — | 2.5 | — | 2.5 | — |
| | g | — | — | — | — | — | — | 2.5 | — | — |

COMPARATIVE EXAMPLE

An enzyme solution D was prepared by incorporating 50 g of polyoxyethylene glycol 400 instead of 50 g of glycerol in the above enzyme solution A, and an enzyme solution E was prepared by incorporating 78 g of ethylene glycol instead of 78 g of glycerol in the above enzyme solution B. These enzyme solutions D and E were diluted with the above diluting solutions a and f as shown in the following Table 4, to prepare treating solutions No. 10 to No. 15. Then, tests for protein removing effects were conducted in the same manner as the above Examples, and the results are shown in Table 4. As is apparent from the results of Table 4, high protein removing effects can be obtained only when glycerol was used as the stabilizer for the enzyme.

TABLE 4

| | | Treating solution No. | | | | | |
|---|---|---|---|---|---|---|---|
| | | 10 | 12 | 12 | 13 | 14 | 15 |
| Enzyme solution (g) | D | 0.05 | — | 0.1 | — | 0.5 | — |
| | E | — | 0.05 | — | 0.1 | — | 0.5 |
| Diluting solution (g) | a | 2.5 | — | — | 2.5 | 2.5 | — |
| | f | — | 2.5 | 2.5 | — | — | 2.5 |
| Protein removing | | 2 | 2 | 2 | 2 | 2 | 1 |

TABLE 4-continued

| | Treating solution No. | | | | | |
|---|---|---|---|---|---|---|
| | 10 | 12 | 12 | 13 | 14 | 15 |
| effects Evaluation | | | | | | |

Further, the respective components were weighed in accordance with the following Table 5 and dissolved in purified water so that the total amount would be 100 g. In this manner, various diluting solutions h to n containing an anionic surfactant having polyoxyethylene glycol units or a nonionic surfactant, were prepared.

TABLE 5

| | | | Diluting solution | | | | | |
|---|---|---|---|---|---|---|---|---|
| | | | h | i | j | k | l | m | n |
| Surfactant (g) | Anionic | Emall 20C*1 | 0.5 | — | — | 0.75 | — | — | — |
| | | SNP-4N*2 | — | 2.5 | — | — | — | — | — |
| | | AKYPO RIM 45NV*3 | — | — | 5.0 | — | — | — | — |
| | | OS-14 | — | — | — | — | — | 0.75 | 0.75 |
| | Nonionic | Nonion HS-220 | — | — | — | 0.5 | 0.5 | 1.5 | 2.5 |
| Viscosity-increasing agent (g) | | Isoban 110 | — | 0.5 | 2.0 | 0.5 | 0.5 | 0.5 | 0.5 |
| Chelating agent (g) | | Crewat N | 0.01 | 0.02 | 0.05 | 0.03 | 0.03 | 0.03 | 0.03 |
| pH | | | 7.0 | 7.5 | 8.0 | 8.5 | 9.0 | 9.0 | 9.0 |

*1: Sodium polyoxyethylene alkyl ether sulfonate, manufactured by Kao Corporation.
*2: Sodium polyoxyethylene (4) nonylphenyl ether sulfonate, manufactured by Nikko Chemicals Co., Ltd.
*3: Sodium polyoxyethylene (4.5) lauryl ether acetate, manufactured by Nikko Chemicals Co., Ltd.

Then, 0.05 g of the above enzyme solution B was diluted with 2.5 g of the above diluting solutions h to n, respectively, to obtain treating solutions No. 16 to No. 22. Using these treating solutions, tests for protein removing effects were conducted in the same manner as in the above Examples, and the results are shown in Table 6.

TABLE 6

| Treating solution No. | 16 | 17 | 18 | 19 | 20 | 21 | 22 |
|---|---|---|---|---|---|---|---|
| Diluting solution | h | i | j | k | l | m | n |
| Protein removing effects Evaluation | 2 | 2 | 2 | 1 | 1 | 3 | 2 |

From the results of Table 6, it is evident that the protein removing effects are extremely poor with treating solutions No. 16 to No. 19 containing surfactants having polyoxyethylene glycol units (Emall 20C, SNP-4N, AKYPO RIM 45NV) even if they are anionic surfactants. Further, the protein removing effects are poor with treating solution No. 20 containing a nonionic surfactant. Further, in a case where a nonionic surfactant is added to an anionic surfactant (OS-14) having no polyoxyethylene glycol unit, the protein removing effects deteriorate when the amount of the anionic surfactant increases excessively.

Further, 0.05 g of the above enzyme solution B was weighed and diluted with 2.5 g of purified water or a physiological sodium chloride aqueous solution. Using treating solution No. 23 or No. 24 thereby obtained, a test for the protein removing effects was conducted in the same manner as the above Examples, whereby with each treating solution, the protein removing effects were very low at a level of Evaluation 1. Thus, it has been found that no adequate protein removal can be accomplished by the action of the protease alone.

Furthermore, 0.05 g of the above enzyme solution B was diluted with 2.5 g of a diluting solution prepared by incorporating 10% by weight of glycerol to the above diluting solution f, to prepare a treating solution No. 25. Using this treating solution, a test for the protein removing effects was conducted in the same manner as the above Examples, whereby the protein removing effects were at a level of Evaluation 3. Thus, it has been found that when the glycerol concentration in the treating solution is high, the cleaning effects tend to be low.

Further, to examine the influence of a metal chelating agent over the cleaning effects, the diluting solution p having Crewat N removed from the components of the above diluting solution f, was prepared. To this diluting solution p, 0.03 g of one of the metal chelating agents shown in the following Table 7 was incorporated. In this manner, various diluting solutions q to t were prepared. Then, 0.05 g of the above enzyme solution B was diluted with 2.5 g of the respective diluting solutions to obtain treating solutions No. 26 to 30. In the same manner as the above Examples, tests for protein removing effects were conducted and the results are shown in Table 7.

TABLE 7

| Treating solution No. | Diluting solution | Metal chelating agent | Protein removing effects Evaluation |
|---|---|---|---|
| 26 | p | (Nil) | 1 |
| 27 | q | Trisodium nitrilotriacetate | 3 |
| 28 | r | Sodium tetrapolyphosphate | 1 |
| 29 | s | Sodium hexametaphosphate | 1 |
| 30 | t | Sodium citrate dihydrate | 2 |

It is evident from the above results that the protein removing effects remarkably deteriorated with the treating solution No. 26 employing the diluting solution p having the ethylene diamine tetraacetate (Crewat N) removed from the diluting solution f. Further, depending upon the type of the metal chelating agent, the protein removing effects by the enzyme substantially differ, and in each of the treating solutions No. 27 to No. 30 employing the diluting solutions q to t, the protein removing effects remarkably deteriorated as compared with the case where the ethylenediamine tetraacetate was used. This indicates that among metal chelating agents, the ethylenediamine tetraacetate has a specific activity to improve the protein removing effects by the enzyme.

Further, tests for protein removing effects were conducted in the same manner as the above Examples using 2.5 g of the above diluting solutions a to g as treating solutions by themselves, the protein soil was not removed at a level of Evaluation 1 in each case.

I claim:

1. A method for cleaning a contact lens, which comprises immersing said contact lens under conditions suitable for and for a time sufficient to clean protein deposits from said lens in a treating solution comprising:
   (A) an enzyme-containing aqueous solution comprising
      (i) a serine protease and
      (ii) from 30 and 95% by weight of glycerol as suitable to stabilize the enzyme during solution storage; and
   (B) a diluting solution comprising
      (i) from 0.05–5% by weight of an anionic surfactant having no polyoxyethylene glycol units and
      (ii) from 0.005–0.1% by weight of ethylenediamine tetraacetate;
   wherein the proportion of (A) to (B) in said treating solution is such that the glycerol concentration is not higher than 5% by weight and the concentration of serine protease is in an amount effective to clean a contact lens.

2. The method for cleaning a contact lens according to claim 1, wherein said diluting solution further comprises from 0.2 to 5% by weight of a copolymer of isobutylene with maleic anhydride or a copolymer of methyl vinyl ether with maleic anhydride.

3. The method for cleaning a contact lens according to claim 1, wherein said enzyme-containing aqueous solution comprises 0.001 to 10% by weight of said serine protease.

4. The method for cleaning a contact lens according to claim 1, wherein said enzyme-containing aqueous solution has a pH of from 6 to 9.

5. The method for cleaning a contact lens according to claim 1, wherein said anionic surfactant having no polyoxyethylene glycol units is selected from the group consisting of 60-olefin sulfonate, alkyl sulfonate, alkylbenzene sulfonate, N-acylamino acid salt and alkyl sulfocarboxylate.

6. The method for cleaning a contact lens according to claim 5, wherein said anionic surfactant having no polyoxyethylene glycol units is selected from the group consisting of sodium tetradecene sulfonate, sodium dodecyl sulfonate, triethanol amine dodecyl sulfonate, sodium dodecylbenzene sulfonate, sodium dioctylsulfosuccinate, sodium cocoilsarycosine and sodium lauroylsarcosine.

7. The method for cleaning a contact lens according to claim 1, wherein said ethylene diamine tetraacetate is selected from the group consisting of disodium ethylenediamine tetraacetate dihydrate and tetrasodium ethylenediamine tetraacetate tetrahydrate.

8. The method for cleaning a contact lens according to claim 1, wherein said diluting solution further comprises a nonionic surfactant in an amount not exceeding the amount of said anionic surfactant.

9. The method for cleaning a contact lens according to claim 8, wherein said nonionic surfactant is selected from the group consisting of polyoxyethylenealkylphenyl ether, polyoxyethylene-polyoxypropylene-block copolymer, polyoxyethylenealkyl ether, alkanol amide and polyoxyethylene sorbitane fatty acid ester.

* * * * *